United States Patent
Nath et al.

(10) Patent No.: US 6,707,297 B2
(45) Date of Patent: Mar. 16, 2004

(54) METHOD FOR IN-SITU EDDY CURRENT INSPECTION OF COATED COMPONENTS IN TURBINE ENGINES

(75) Inventors: Shridhar Champaknath Nath, Niskayuna, NY (US); Thomas James Batzinger, Burnt Hills, NY (US); Curtis Wayne Rose, Mechanicville, NY (US); Yuri Alexeyevich Plotnikov, Clifton Park, NY (US); Kenneth Gordon Herd, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 53 days.

(21) Appl. No.: 10/122,836

(22) Filed: Apr. 15, 2002

(65) Prior Publication Data

US 2003/0193331 A1 Oct. 16, 2003

(51) Int. Cl.$^7$ .......................... G01N 27/82; G01N 27/90
(52) U.S. Cl. ........................................ 324/240; 324/238
(58) Field of Search ................................ 324/240–243, 324/238, 219–221, 261, 262, 226, 232, 227; 73/661, 779

(56) References Cited

U.S. PATENT DOCUMENTS

| | | | |
|---|---|---|---|
| 4,048,558 A | * | 9/1977 | Goodman .................... 324/609 |
| 4,414,508 A | * | 11/1983 | Davis et al. ................. 324/238 |
| 4,468,620 A | | 8/1984 | Vaerman |
| 4,644,274 A | | 2/1987 | Casarcia |
| 4,929,896 A | * | 5/1990 | Lara ............................ 324/240 |
| 5,015,950 A | * | 5/1991 | Rose et al. .................. 324/224 |
| 5,140,264 A | * | 8/1992 | Metala et al. ............... 324/219 |
| 5,152,058 A | | 10/1992 | Legros |
| 5,391,988 A | * | 2/1995 | Kitagawa .................... 324/225 |
| 5,442,285 A | * | 8/1995 | Zombo et al. ............... 324/227 |
| 5,442,286 A | | 8/1995 | Sutton, Jr. et al. |
| 5,781,007 A | | 7/1998 | Partika et al. |
| 6,037,768 A | | 3/2000 | Moulder et al. |
| 6,534,975 B2 | | 3/2003 | Beeck et al. |

OTHER PUBLICATIONS

Y. A. Plotnikov, S. C. Nath & C. W. Rose, "Defect Characterization in Multi–Layered Conductive Components with Pulsed Eddy Current", Review of Quantitative Nondestructive Evaluation, vol. 21, 2002 American Institute of Physics, pp. 1976–1977.

H. A. Sabbagh, E. H. Sabbagh, R. Kim Murphy, "Applications of Eddy–Current Inversion", Victor Technologies, LLC, pp. 149–150.

G. Antonelli, P. Crisafulli, G. Tirone, Qualification of a Frequency Scanning Eddy Current Equipment for Nondestrictive Characterization of New and Serviced High–Temperature Coatings, ASME Turbo EXPO 2001, Jun. 4–7, 2001, New Orleans, Louisiana, USA, pp. 1–2.

* cited by examiner

Primary Examiner—N. Le
Assistant Examiner—Reena Aurora
(74) Attorney, Agent, or Firm—Penny A. Clarke; Patrick K. Patnode

(57) ABSTRACT

A method for in-situ eddy current inspection of at least one coated component includes applying a drive pulse at a measurement position on an outer surface of the coated component, while the coated component is installed in an operational environment of the coated component. The coated component includes a base metal and a coating disposed on the base metal. The method further includes receiving a response signal from the coated component, comparing the response signal with a reference signal to obtain a compared signal, analyzing the compared signal for crack detection, and determining whether a crack near the measurement position has penetrated into the base metal, if the presence of the crack in the coating is indicated.

30 Claims, 10 Drawing Sheets

METHOD FOR IN-SITU EDDY CURRENT INSPECTION OF COATED COMPONENTS IN TURBINE ENGINES

BACKGROUND OF THE INVENTION

The invention relates generally to in-situ inspection of coated components and, more particularly, to in-situ eddy current inspection of coated components in turbine engines, for example airfoils in gas turbine engines and coated turbo components in locomotive diesel engines.

A gas turbine engine typically includes a compressor that supplies pressurized air to a combustor. The air is mixed with fuel in the combustor and ignited to generate hot combustion gases. The hot gases flow downstream to one or more turbines that extract energy from the hot gases to power the compressor and provide useful work, such as generating power at a power plant or powering an aircraft in flight.

Each turbine stage typically includes a turbine rotor assembly and a stationary turbine nozzle assembly for channeling combustion gases into the turbine rotor assembly disposed downstream therefrom. The turbine rotor assembly 50 commonly includes a number of circumferentially spaced apart rotor blades 20 extending radially outwardly from a rotor disk 30 that rotates about the rotor 10, as illustrated schematically in FIG. 1. Rotor blades generally include airfoils (also indicated by reference numeral 20) and are commonly called "buckets" for land based turbine engines. As used here, the term "blade" encompasses "buckets" as well as blades. The rotor assembly is housed within a case 40.

The stationary turbine nozzle assembly 60 includes a number of circumferentially spaced apart stationary vanes 21 radially aligned with the rotor blades 20, as schematically illustrated in FIG. 2. The stationary vanes are disposed between inner and outer bands 42, 41. The stationary vanes include airfoils (indicated by reference numeral 21 in FIG. 2) and are configured to direct the hot combustion gases to the downstream turbine rotor assembly, and, more particularly, toward the rotor blades 20. Vanes are commonly called "nozzles" for land based turbine engines, and as used here the term "vane" encompasses both vanes and nozzles.

An exemplary airfoil 20 is illustrated in FIG. 3 in cross-sectional view and includes a base metal 24, for example formed of nickel superalloys, such as GTD111 or IN738. The core can be hollow or solid. The core is coated for protection against erosion and to render the airfoil suitable for use in high temperatures, with exemplary protective coatings 22 being NiCoCrAlY or MCoCrAlY. In addition, the airfoil may also include an outer ceramic coating 23, to act as a thermal barrier (hereinafter a "thermal barrier coating").

In response to the stress induced by thermal gradients in the airfoils and other operating conditions in gas turbine engines, cracks can develop in the airfoil coatings. An exemplary crack 52 is indicated in FIG. 3. Although cracks generally terminate at the diffusion zone between the protective coating and the base metal, cracks do occasionally penetrate into the base metal.

In order to inspect airfoils for cracks, presently airfoils are removed from the rotor assembly and from the nozzle assembly during outage cycles for inspection, refurbishment, and determination of the remaining lives of the airfoils. The outage cycles occur about every 24,000 to 30,000 operational hours. In the current inspection process, the airfoils are first inspected by fluorescent penetrant inspection, to detect cracks in the coatings. When cracks are detected, the cracked airfoil is hand blended using a hand-held grinder to remove the cracks. A final fluorescent penetrant inspection is conducted to confirm that the cracks have been removed.

One drawback to the present airfoil inspection method is that removal of the airfoils from the rotor assembly and from the nozzle assembly and the subsequent fluorescent penetrant inspection of the airfoils are time and labor intensive, contributing to long and expensive gas turbine outages. In addition, the fluorescent penetrant inspection method detects only the presence of a crack and does not determine whether the crack is localized within the coatings 22, 23 or has penetrated the base metal 24, nor does the existing inspection method determine the depth of the crack. Moreover, the grinding performed while chasing the cracks progresses to the base metal in many instances, undesirably reducing the wall thickness of the airfoil.

Accordingly, it would be desirable to develop a method for in-situ inspection of gas turbine airfoils to determine the presence of cracks in the airfoils. It would further be desirable for the method to determine the crack depth and whether the crack has penetrated the base metal of the airfoil. In addition, it would be desirable for the method to employ nondestructive inspection techniques.

BRIEF DESCRIPTION OF THE INVENTION

Briefly, in accordance with one embodiment of the present invention, a method for in-situ eddy current inspection of at least one coated component is disclosed. The coated component includes a base metal and a coating disposed on the base metal. The method includes applying a drive pulse at a measurement position on an outer surface of the coated component, while the coated component is installed in an operational environment of the coated component. The method further includes receiving a response signal from the coated component, comparing the response signal with a reference signal to obtain a compared signal, analyzing the compared signal for crack detection, and determining whether a crack near the measurement position has penetrated the base metal, if the presence of the crack in the coating is indicated.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
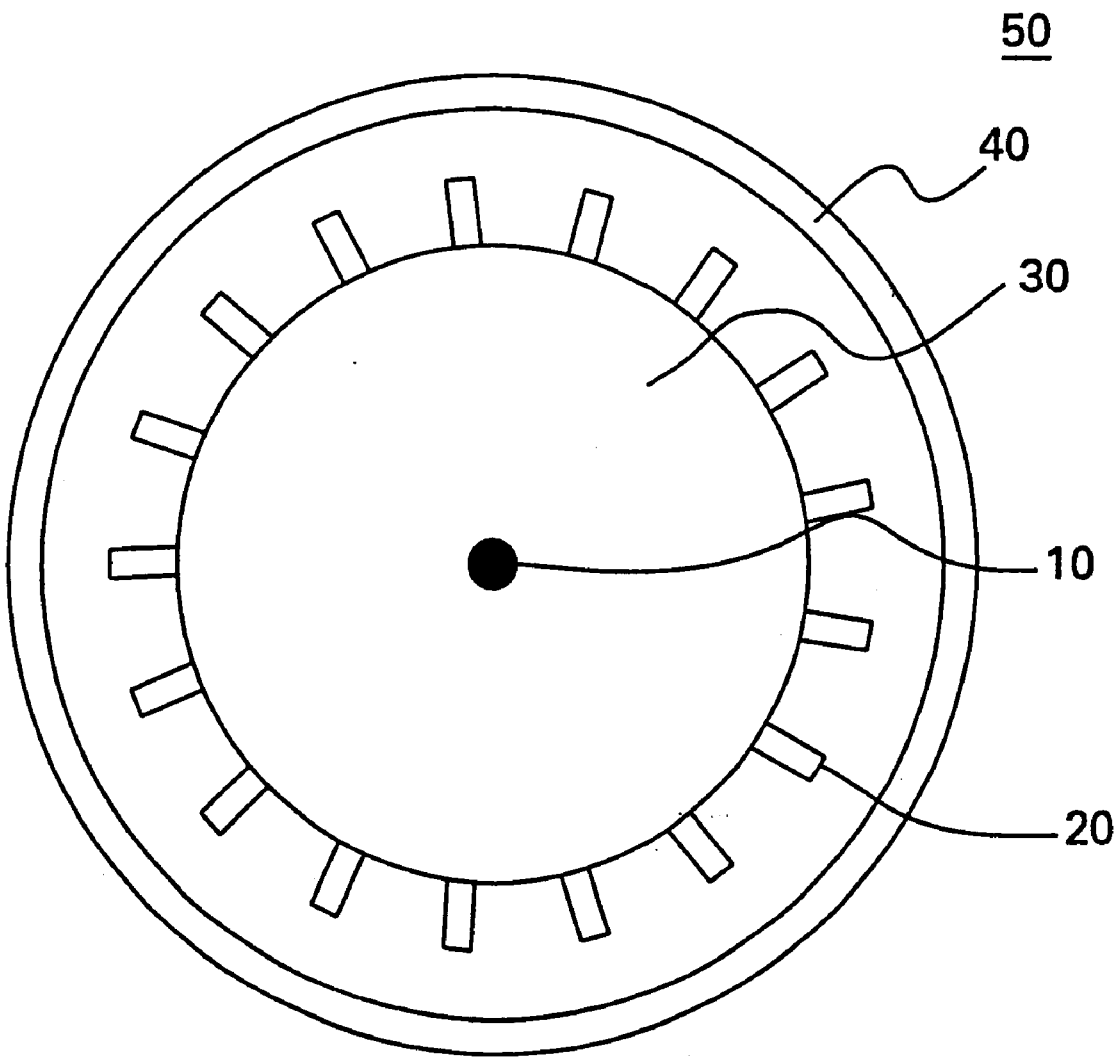
FIG. 1 schematically depicts basic elements of a turbine rotor assembly, in cross-sectional view.

A method for in-situ eddy current inspection of at least one coated component 20, is explained with reference to FIGS. 4 and 5. As used here, the phrase "in-situ" means that the inspection is performed while the coated component 20 is installed in its operational environment typically while the operational environment is not running. For example, "in-situ" eddy current inspection of an airfoil (also indicated by reference numeral 20) is performed while airfoil 20 is mounted in a turbine engine (not shown) and typically while the turbine engine is not running. Similarly, "in-situ" eddy current inspection of a coated turbo component (not shown) is performed while the coated turbo component is mounted in a locomotive diesel engine (not shown). The in-situ inspection method includes applying a drive pulse at a measurement position 28 on an outer surface 11 of coated component 20. Coated component 20 includes a base metal 24 and a coating 22, as exemplarily shown for an airfoil 20 in FIG. 3. Exemplary airfoils 20 include stationary airfoils (indicated by reference numeral 21 in FIG. 2) mounted in nozzle assemblies 60 and rotating airfoils (also indicated as 20) mounted in rotor assemblies 50, as discussed above and as shown for example in FIGS. 1 and 2.

Exemplary drive pulses include electromagnetic pulses. An exemplary application of a drive pulse includes energizing a drive coil 12 with a pulse of electrical current, drive coil 12 being positioned at measurement position 28, as schematically indicated in FIG. 4. For example, a pulse generator 70 supplies a fixed duration pulse to drive coil 12, as shown for example in FIG. 4. The fixed duration pulse comprises a continuum of frequencies, and because penetration depth depends on the excitation frequency, use of a fixed duration pulse provides information from a range of depths. Exemplary drive pulses have a pulse width of about 10 μs to about 100 μs, and more particularly, about 20 μs. Still more particularly, the drive pulse is a square wave pulse (or more generally a rectangular wave pulse), for example having a pulse width of about 20 μs. Other exemplary drive pulses include delta function pulses and sawtooth pulses, and the inventive method is not limited to any particular pulse waveform. Optimal drive pulse amplitudes vary based on the materials forming drive coil 12, magnetic field sensor 14, and coated component 20.

Exemplary drive coils 12 include eddy current coils. Eddy current coils are conductive coils with a variety of coil diameters and turn numbers. An exemplary eddy current coil is formed from copper and has a coil diameter of about 5 mm to about 25 mm. Other exemplary eddy current coils include single eddy current array probes (SECAPs) (not shown). SECAPs are single, conducting coils formed on a flexible substrate by known photolithographic methods. A variety of conductive materials, such as copper, silver, and gold are used to form SECAPS.

Figure 4:
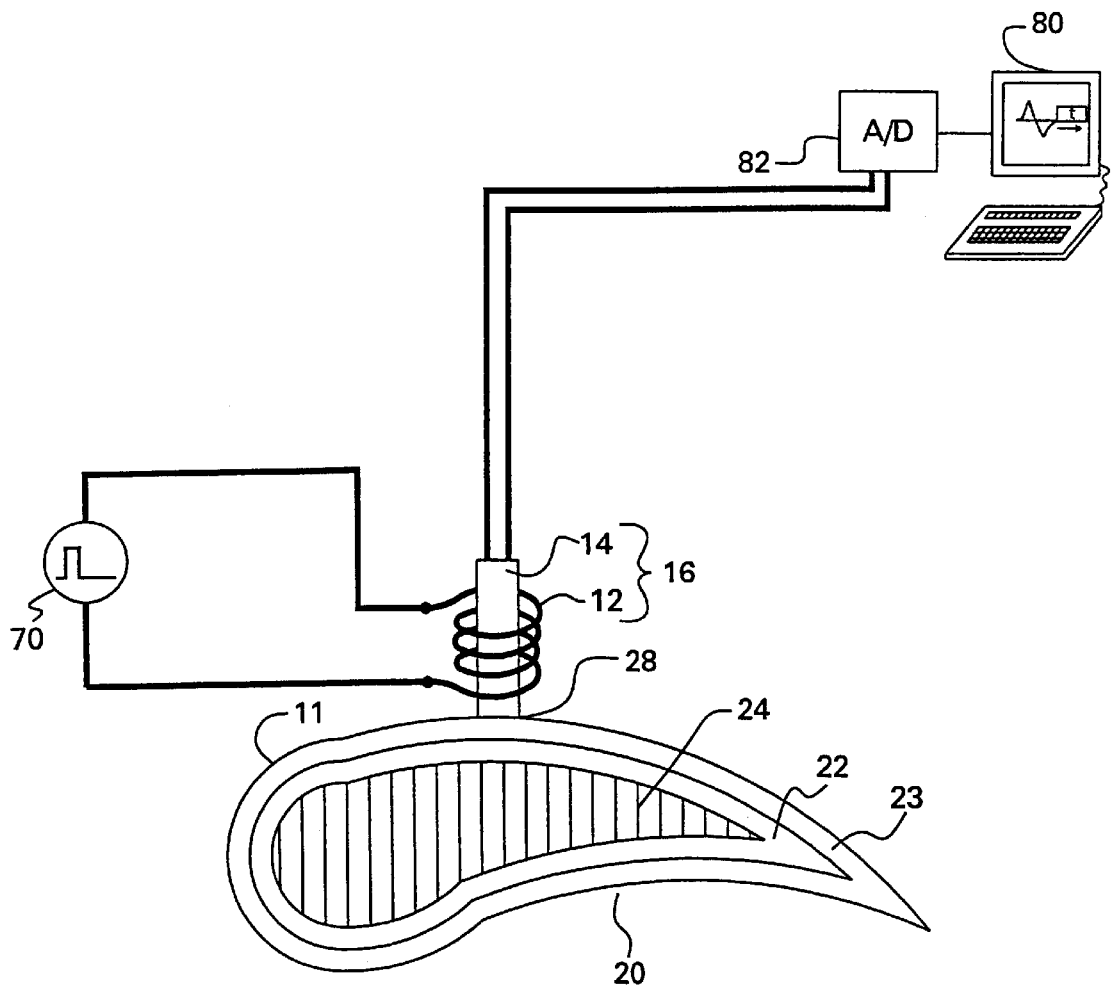
FIG. 4 schematically illustrates a system for implementing a method for in-situ eddy current inspection of coated components.
Figure 5:
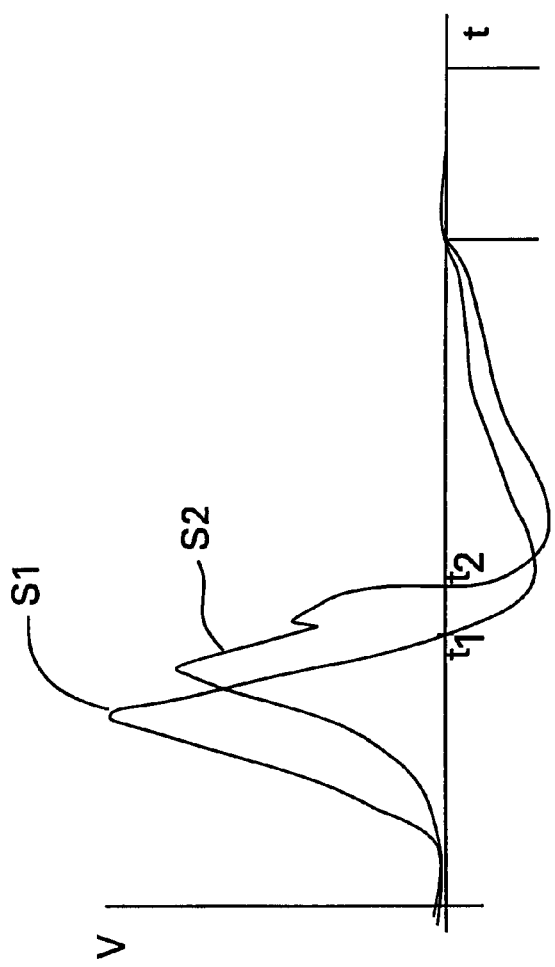
FIG. 5 depicts a drive pulse, a differential signal signifying a crack free measurement, and a differential signal indicating the detection of a crack, all signals being shown as a function of time.
Figure 5:
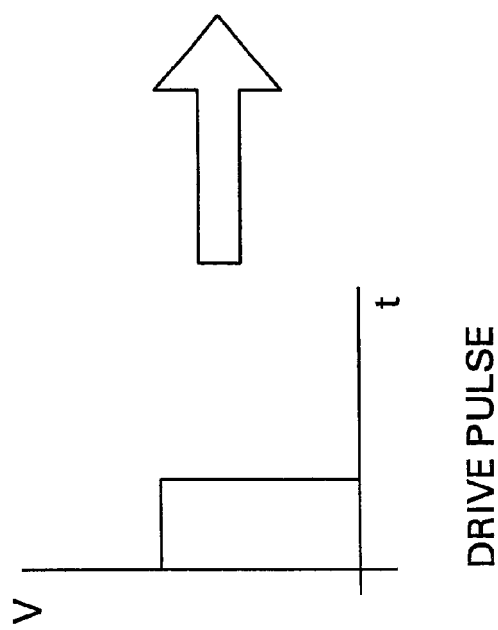

The in-situ eddy current inspection method further includes receiving a response signal from coated component 20, for example receiving the response signal with a magnetic field sensor 14 positioned at measurement position 28 on outer surface 11 of coated component 20, as schematically indicated in FIG. 4. As used herein, the phrase "on outer surface 11 of coated component 20" means in close proximity to outer surface 11, such that the drive pulse induces eddy currents in coated component 20 and such that magnetic field sensor 14 detects the secondary magnetic fields generated by the eddy currents in coated component 20. Exemplary magnetic field sensors 14 include a sense coil (not shown) such as a SECAP or conventional eddy current coil, a Hall element, or a giant magnetoresistive (GMR) sensor. These devices are known and hence will not be described further.

For compactness and ease of use, drive coil 12 and magnetic field sensor 14 are combined, in a particular embodiment, to form a single sensor unit, which is indicated by reference numeral 16 in FIG. 4.

The response signal is based on the secondary magnetic fields and is a time domain response signal, namely it is transient. In more detail, the drive pulse generates a primary magnetic field, which induces eddy currents within the conductive elements (base metal 24 and conductive protective coating 22) of coated component 20. The eddy currents in turn generate the secondary magnetic fields. However, the presence of a crack 52 in coated component 20 (namely, in protective coating 22 or base metal 24) changes the flow of the eddy currents within coated component 20. The altered eddy current, in turn, produces a modified secondary magnetic field, which is detected by magnetic field sensor 14, thereby generating a response signal, which reflects the presence of crack 52.

Figure 10:
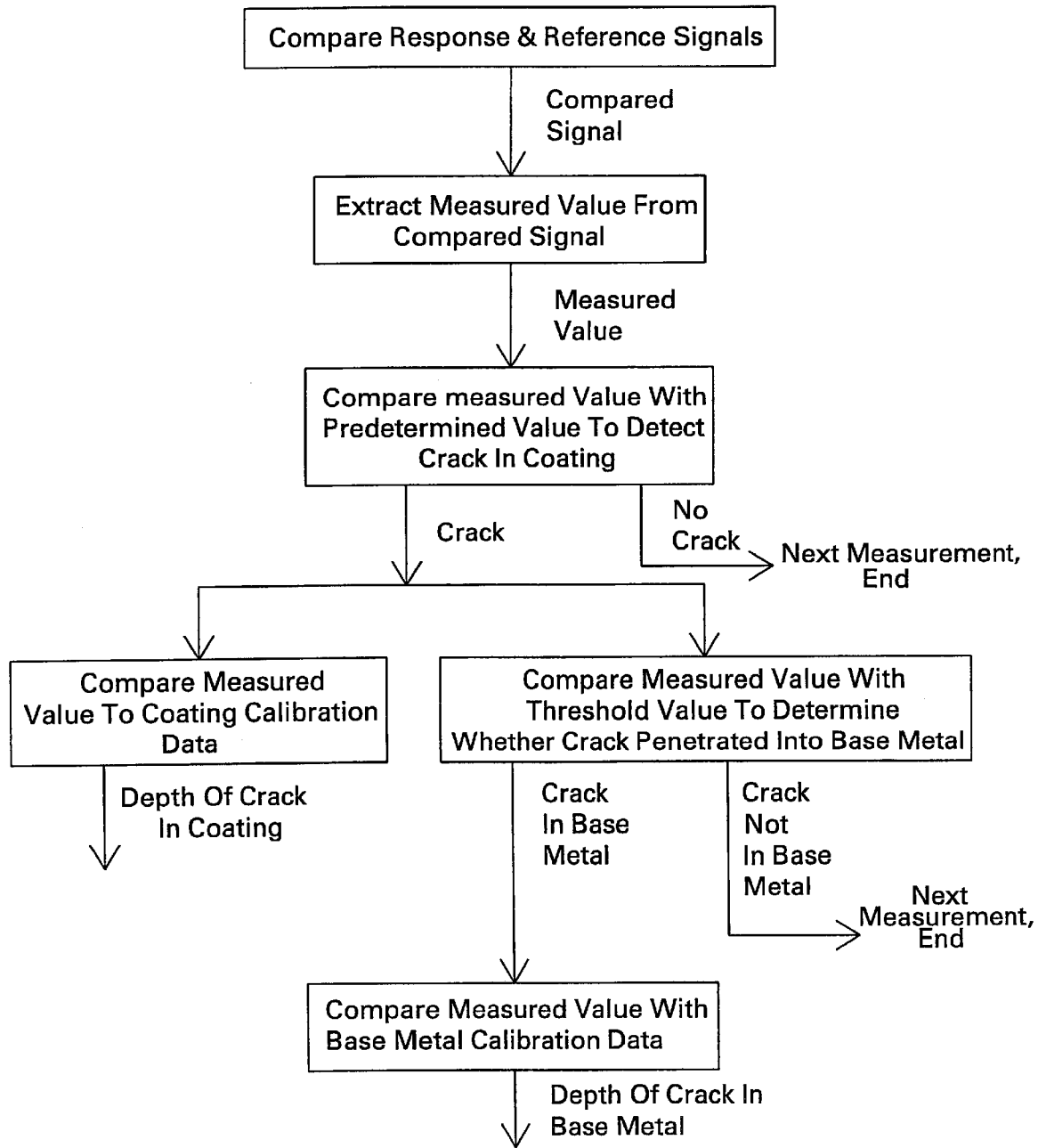
FIG. 10 illustrates exemplary crack detection and crack depth determination processes of the inventive method for in-situ eddy current inspection of coated components.

The in-situ eddy current inspection method further includes comparing the response signal with a reference signal to obtain a compared signal, as indicated in FIG. 10. The reference signal is also a time-domain signal (i.e., transient). More particularly, the compared signal is obtained by subtracting the reference signal from the response signal. Exemplary compared signals are shown in FIG. 5 to illustrate the general shape of compared signals obtained using the inventive method. As shown in FIG. 5, the differential signals change with time and are related to the thickness of the airfoil at measurement position 28. The larger amplitude differential signal S1 corresponds to a measurement with no crack, and the smaller amplitude differential signal S2 reflects the presence of crack 52 in airfoil 20. Exemplary means for comparing the response signal with the reference signal include an oscilloscope (not shown) and a data acquisition system 80, such as a computer 80, as schematically indicated in FIG. 4.

The in-situ eddy current inspection method further includes analyzing the compared signal for crack detection. In addition, the inspection method includes determining whether a crack 52 near the measurement position 28 has penetrated base metal 24, if the presence of crack 52 is indicated. In this manner, the inspection method determines whether crack 52 has penetrated into base metal 24 or is localized in coating 22. Exemplary means for analyzing the compared signal and for ascertaining base metal penetration include data acquisition system 80, shown in FIG. 4.

To obtain the reference signal, the in-situ eddy current inspection method according to one embodiment also includes positioning drive coil 12 and magnetic field sensor 14 at a reference position on an outer surface of a reference sample (not shown), energizing drive coil 12 with a drive pulse, and receiving the reference signal with magnetic field sensor 14. The reference signal is stored for comparison with the response signal, for example in computer data acquisition system 80. According to a particular embodiment, the reference sample has the same structure and material characteristics as coated component 20, prior to the operational use of coated component 20. For example, both coated component and the reference sample include base metal 24 and coating 22. However, reference sample is crack free near the reference position, whereas coated component 20 may or may not be crack free at measurement position 28. According to more particular embodiments, the reference position on the reference sample either coincides with measurement position 28 on coated component 20 or corresponds to a coating thickness on reference sample that is about the same as the original coating thickness at measurement position 28 (i.e., the coating thickness prior to use of coated component 20, for example in a turbine engine).

Figure 9:
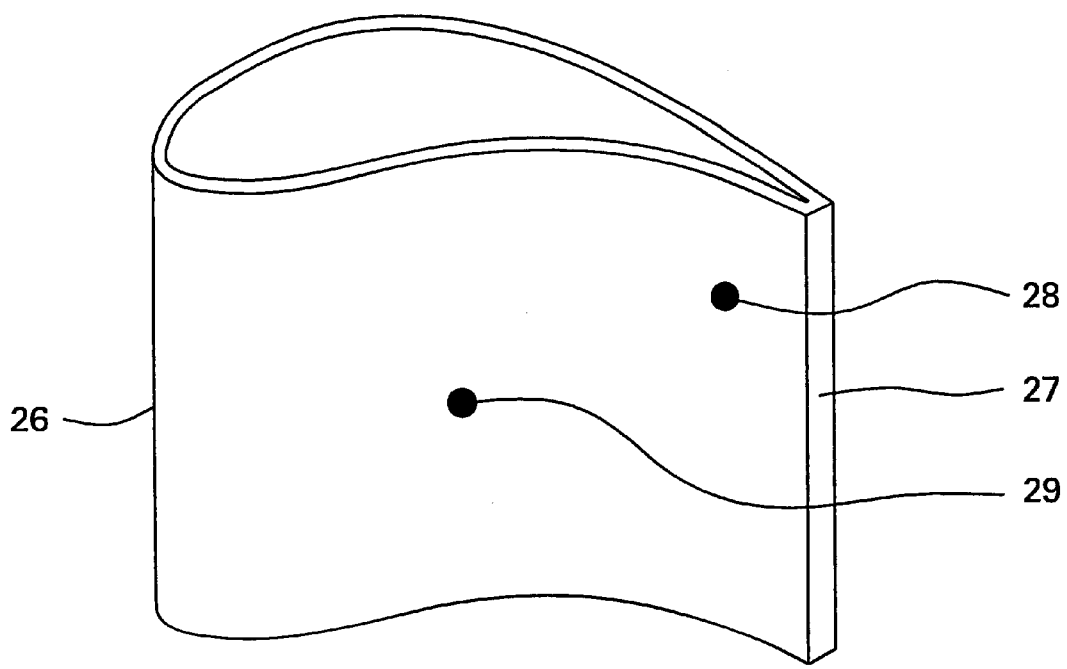
FIG. 9 shows exemplary measurement and reference positions on an exemplary airfoil.

An alternative embodiment is illustrated in FIG. 9 for which the reference signal is obtained by applying a drive pulse at a same-sample reference position 29 on coated component 20, while coated component 20 is installed in its operational environment, for example while airfoil 20 is mounted in turbine engine (not shown), and receiving the reference signal with a reference magnetic field sensor (not shown) at same-sample reference position 29. By "same-sample," it is meant that both the reference and the measurement positions 28, 29 are on the same coated component 20, as shown for example in FIG. 9. Same-sample reference position 29 is selected using historical data and additionally or alternatively using experience, such that cracking is unlikely to occur at same-sample reference position 29. For a coated component 20 with a varied coating thickness, same-sample reference position 29 is further selected such that the coating thickness at measurement position 28 and same-sample reference position 29 is about the same. Advantageously, for same-sample referencing, the reference signal is not affected by the temperature inside the turbine engine because the response signal and reference signal are obtained in the same general area. However, the embodiment employing the reference sample is advantageous in that only drive coil 12 and magnetic field sensor 14 or, more particularly, only sensor unit 16 need be inserted into the operational environment for coated component 20.

For a coated component 20 with a uniform coating thickness, the reference signal so obtained is stored, for example in computer data acquisition system 80, for comparison with one or more response signals. For a coated component 20 with a varied coating thickness, reference signals are obtained at a number of reference positions on a separate sample (or at a number of same-sample reference positions 29 on coated component 20) having coating thicknesses about the same as the coating thicknesses at the measurement positions 28.

For signal processing purposes, the in-situ eddy current inspection method according to another embodiment additionally includes digitizing the reference signal and the response signal to obtain a digitized reference signal and a digitized response signal, respectively. Exemplary digitization means include an analog-to-digital converter 82, as indicated schematically in FIG. 4. The digitized reference and response signals are compared by subtracting the digitized reference signal from the digitized response signal, to obtain a digitized differential signal. Exemplary comparison means include computer data acquisition system 80.

To obtain a more accurate response signal, the in-situ eddy current inspection method according to another embodiment averages the digitized response signal over several (for example, five) measurements. More particularly, a drive pulse is applied at measurement position 28 several times and a corresponding number of response signals are received with magnetic field sensor 14 situated at measurement position 28. The response signals are digitized to obtain a number of digitized signals. According to one embodiment, the digitized reference signal is subtracted from each of the digitized signals to obtain a number of digitized compared signals, which are averaged to obtain the compared signal. Alternatively, the digitized signals can be averaged to obtain the digitized response signal. For the latter embodiment, the comparison involves subtracting the digitized reference signal from the digitized response signal to obtain the compared signal, as discussed above.

In one embodiment of the in-situ eddy current inspection method, crack detection analysis is performed by extracting a measured value from the compared signal, as indicated in FIG. 10. For example a time value t or peak amplitude value V is extracted from the compared signal. The measured value is compared with a predetermined value to determine the presence of a crack 52 near the measurement position 28, as indicated in FIG. 10. According to this embodiment, ascertainment of base metal penetration includes comparing the measured value with a threshold value to determine whether the crack 52 has penetrated the base metal 24.

Exemplary measured values include time values and peak amplitude values. Time values characterize the behavior of the differential signal with time. One exemplary time value is the time at which the differential signal crosses V=0 (denoted by t). The time values t are indicated in FIG. 5 for the two differential signals S1 and S2. Of course other time value schemes could be selected, for example the time at which the differential signal has its peak amplitude could be employed, as could the time at which the differential signals cross a designated voltage $V_o$.

Exemplary predetermined values are extracted from differential signals corresponding to crack free measurements. For such predetermined values, deviation of the measured value from the predetermined value indicates the presence of a crack, as discussed in greater detail below. Alternatively, the predetermined value may be extracted from differential signals corresponding to the presence of a crack. For the latter type of predetermined value, coincidence of the measured and predetermined values indicates the presence of a crack. The type of predetermined value or threshold value follows from the type of measured value employed. Namely, a predetermined (or threshold) time value is compared with a time value, while a predetermined (or threshold) peak amplitude value is compared with a peak amplitude value. An exemplary predetermined time value could be determined as follows. Where the time value is selected to be the time at which the differential signal crosses V=0, the value $t_1$, shown in FIG. 5 could serve as a predetermined time value because the differential signal S1 corresponds to a crack-free measurement. Exemplary threshold values are discussed below with respect to FIGS. 6 and 7.

Figure 7:
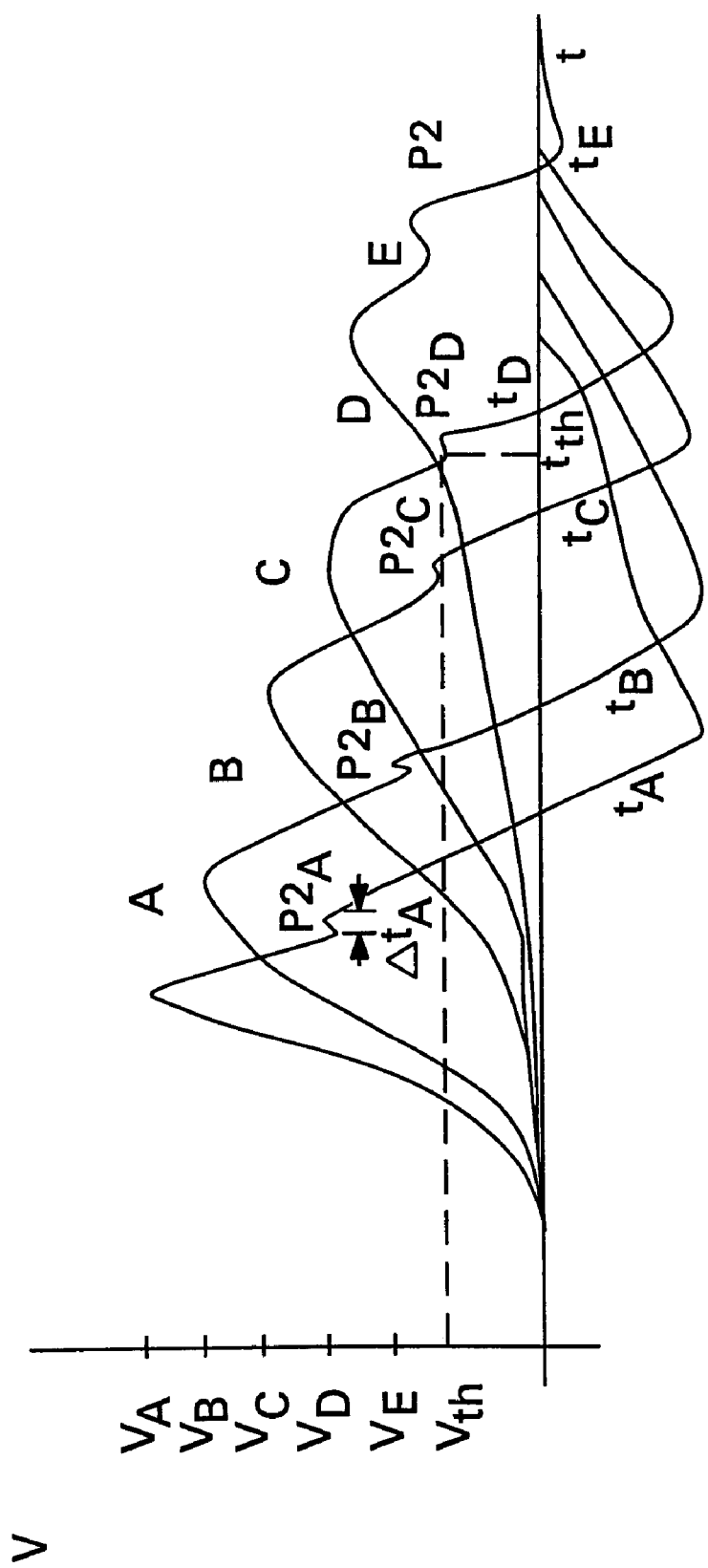
FIG. 7 shows a set of illustrative differential signals corresponding to the series of notches illustrated in FIGS. 6a–e.

As noted above, another measured value of the differential signal is the peak amplitude value. As shown in FIGS. 5 and 7, peak amplitude of the difference signal is reduced by the presence of a crack near measurement position 28. An exemplary predetermined peak amplitude value is the peak amplitude of the differential signal S1, which corresponds to a crack-free measurement.

Where the predetermined value is extracted from a differential signal S1 that corresponds to a crack-free measurement, the measured value is compared with the predetermined value as follows. Where the measured value is a time value t, the presence of a crack near measurement position 28 is indicated if the time value exceeds the predetermined time value (or exceeds the predetermined time value plus an incremental amount δt, such as the measurement error for the time values). Where the measured value is the peak amplitude value V, the presence of a crack near measurement position 28 is indicated if the peak amplitude value is less than the predetermined peak amplitude value (or less than the predetermined peak amplitude value less an incremental amount δV, such as the measurement error for the peak amplitude values).

In order to ascertain whether crack 52 has penetrated base metal 24, the measured value is compared with the threshold value, as noted above and as indicated in FIG. 10. FIG. 6d shows crack 52 beginning to penetrate base metal 24. Illustrative signal D in FIG. 7 corresponds to the crack formation shown in FIG. 6d. Accordingly, exemplary threshold values are the time $t_D$ at which signal D crosses V=0 and peak amplitude value $V_D$. Thus, exemplary comparisons of the measured value with the threshold value include the following. For a measured value t, the penetration of crack 52 into base metal 24 near measurement position 28 is indicated if t>$t_D$ (or t>($t_D$+δt)). For a measured value V, the penetration of crack 52 into base metal 24 near measurement position 28 is indicated if V<$V_D$ (or V<($V_D$+δV)).

In addition to detecting the presence of a crack 52 near measurement position 28 and ascertaining whether crack 52 has penetrated base metal 24, it is desirable to determine the depth of crack 52. Accordingly, a specific embodiment of the inventive method further includes performing crack depth analysis for coating 22, if the crack detection analysis indicates the presence of crack 52 near measurement position 28. In order to determine the depth of crack 52 in coating 22, according to a more specific embodiment, the measured value for the compared signal is compared with a set of coating calibration data, as indicated in FIG. 10. Exemplary coating calibration data are obtained by performing a series of pulsed eddy current measurements on a calibration coated component (also indicated by reference numeral 20) with a progressively deeper crack 52 in coating 22, as exemplarily illustrated in FIGS. 6a–c. Corresponding compared signals A–C are illustrated in FIG. 7. Of course the number of calibration cracks (here 3) and crack depths shown are purely illustrative. Instead, the number of calibration data points will vary depending on the desired accuracy for the crack depth measurements, with more calibration data points (and corresponding calibration crack depths) needed to achieve higher accuracy. According to a particular embodiment, calibration coated component includes the same base metal 24 and coating 22, as the coated component 20 being inspected because the coating calibration data depends on both the constituent material and thickness of coating 22 and base core 24. According to a more particular embodiment, the coating calibration data and the response signal are obtained at about the same temperature and about the same lift off. As used here, the term "lift off" refers to the separation between sensor unit 16 and the measurement sample, for example coated component 20.

Figure 6A:
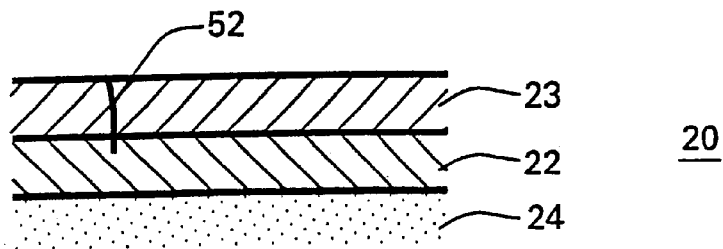
FIGS. 6a–e show an exemplary series of known notches of varying depth in a coated component, which can be measured to obtain crack length calibration data.
Figure 6B:
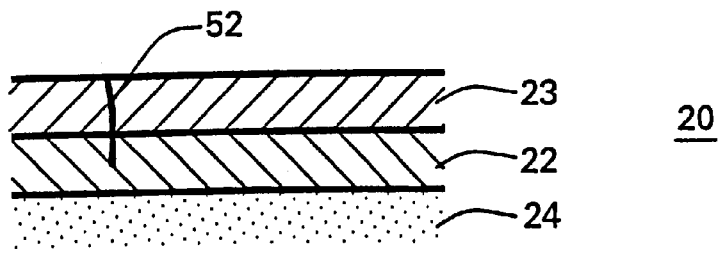
Figure 6C:
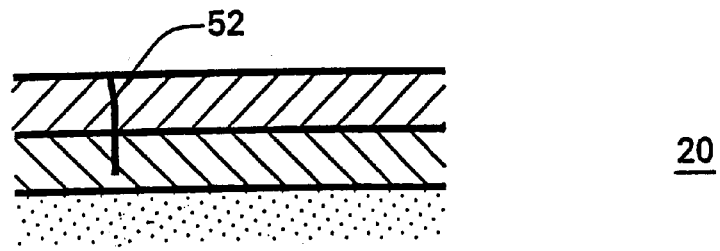
Figure 6D:
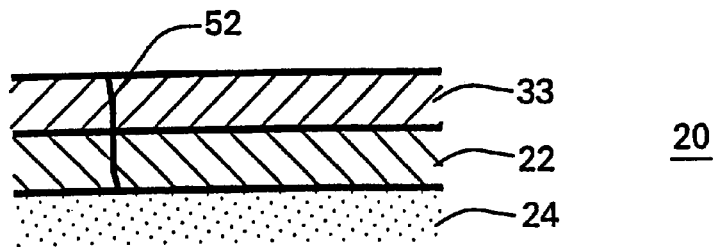

In order to obtain coating calibration data, an exemplary crack progression can be obtained by stepwise etching (using etchants that selectively etch in a direction normal to the surface of the coated component) or drilling the calibration coated component 20 to achieve a series of known notches of varying depth in coating 22, as shown for example in FIGS. 6a–c. For example known notches of varying depth are obtained by performing electrical discharge machining (EDM) or electrochemical machining (ECM), respectively. After each crack forming step, the crack depth is measured, for example using drive coil 12 and magnetic sensor 14, to obtain a compared signal such as the illustrative signals A–C shown in FIG. 7, and is additionally measured using known methods to calibrate the compared signals. Exemplary known, crack depth measurement methods include using an optical gage (not shown). Alternatively, cracks can be formed in different calibration coated components 20 or at different positions on one calibration coated component, and the pulsed eddy current and standard measurements can be performed for each crack as described. In this manner, exemplary coating calibration data such as exemplary time values $t_A$–$t_C$ and exemplary peak amplitude values $V_A$–$V_C$ indicated on FIG. 7 are obtained, each of which corresponds to a specific crack depth in coating 22, measured by the known method. Thus for these embodiments, comparison of the measured value time value t (or peak amplitude value V) obtained from the in-situ measurements with the coating calibration data includes comparing time value t (or peak amplitude value V) with calibration data $t_A$–$t_C$ (or $V_A$–$V_C$). In this manner, the depth of crack 52 in coating 22 is determined.

Where crack 52 has penetrated base metal 24, it is further desirable to determine the depth of crack 52 in base metal 24, in order to determine the extent of the damage to coated component 20. Such information is useful to determine whether or not time consuming and costly repair operations should be performed on a damaged coated component, to reduce the number of futile repair operations undertaken on overly damaged coated components. Accordingly, another embodiment of the inventive method further includes performing crack depth analysis for base metal 24, if the penetration of base metal by crack 52 is ascertained. In order to determine the depth of crack 52 in base metal 24, according to a more specific embodiment, the measured value for the compared signal is compared with a set of base metal calibration data, as indicated in FIG. 10.

Figure 6E:
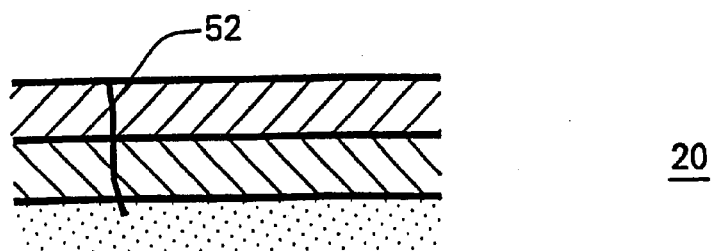

Similar to the procedure for obtaining coating calibration data discussed above, exemplary base metal calibration data are obtained by performing a series of pulsed eddy current measurements on a calibration coated component (also indicated by reference numeral 20) with a progressively deeper crack 52 in base metal 24, as exemplarily illustrated in FIGS. 6d and 6e. More particularly, an exemplary crack progression (for example, a set of EDM notches) can be obtained by performing EDM on coated component(s) 20, as discussed above. By comparing the resulting compared signals D and E in FIG. 7 with crack depth measurements performed using known means, such as an optical gage, the measured values for signals D and E (i.e., $t_D$ and $t_E$ or $V_D$ and $V_E$) are calibrated, providing the base metal calibration data. Accordingly, comparison of measured time value t (or peak amplitude value V) obtained from the in-situ measurements with the base metal calibration data $t_D$ and $t_E$ (or $V_D$ and $V_E$) determines the depth of crack 52 in base metal 24. Of course the number of base metal calibration data points (here two) shown is purely illustrative and for convenience. The desired number of base metal calibration data points will be determined based on the desired accuracy of the crack depth determination for base metal 24, with more data points being needed to achieve higher accuracy.

In another embodiment of the in-situ eddy current inspection method, crack detection analysis is performed by determining whether the compared signal includes a secondary peak P2. This embodiment is particularly beneficial for crack orientations that are not perpendicular to the surface of coated component 20 and also for coated components with a number of cracks in close proximity to one another. An illustrative secondary peak P2 is shown in FIG. 5. Although the secondary peak P2 is generally on the trailing edge of the compared signal and is illustrated as such in FIGS. 5 and 7, it is also possible for the secondary peak P2 to appear on the leading edge thereof. Specifically, the presence of a secondary peak P2 indicates the presence of a crack 52 near measurement position 28. Determination that the compared signal includes a secondary peak can be performed by detecting a change in curvature within the compared signal, for example by evaluating the second derivative of the compared signal using data acquisition system 80. Alternatively, multiple peak detection, first derivative, or second derivative analysis can be performed.

According to this embodiment, ascertainment of base metal penetration includes determining a signature value for the secondary peak P2 and comparing the signature value with a threshold value to determine whether crack 52 has penetrated base metal 24. Exemplary means for determining the signature value and performing the comparison include computer data acquisition system 80.

The secondary peak P2 varies based on the depth of crack 52 and whether crack 52 has penetrated base metal 24, as illustrated by FIGS. 6 and 7. Briefly, a progression of crack 52 is shown in FIGS. 6a–6e and corresponding compared signals A–E are illustrated in FIG. 6. As illustrated in FIG. 7, the amplitude V, time at which the secondary peak appears t, and width Δt (for example the full width at half maximum) of secondary peak P2 vary with the depth of crack 52 and whether crack 52 extends into base metal 24 or is localized within coating 22. Accordingly, exemplary signature values for secondary peak P2 include amplitude V, time at which secondary peak P2 appears, and width Δt.

As discussed above, illustrative signal D in FIG. 7 corresponds to crack 52 beginning to penetrate base metal 24, as shown in FIG. 6d, and thus to a threshold signal. Accordingly, exemplary threshold values are the time $t_{th}$ at which secondary peak $P2_D$ appears and peak amplitude value $V_{th}$ of secondary peak $P2_D$. Thus, exemplary comparisons of the signature with the threshold value include the following. For a signature value t, the penetration of crack 52 into base metal 24 near measurement position 28 is indicated if $t > t_{th}$ (or $t > (t_{th} + \delta t)$). For a signature value V, the penetration of crack 52 into base metal 24 near measurement position 28 is indicated if $V < V_{th}$ (or $V < (V_{th} + \delta V)$).

Figure 2:
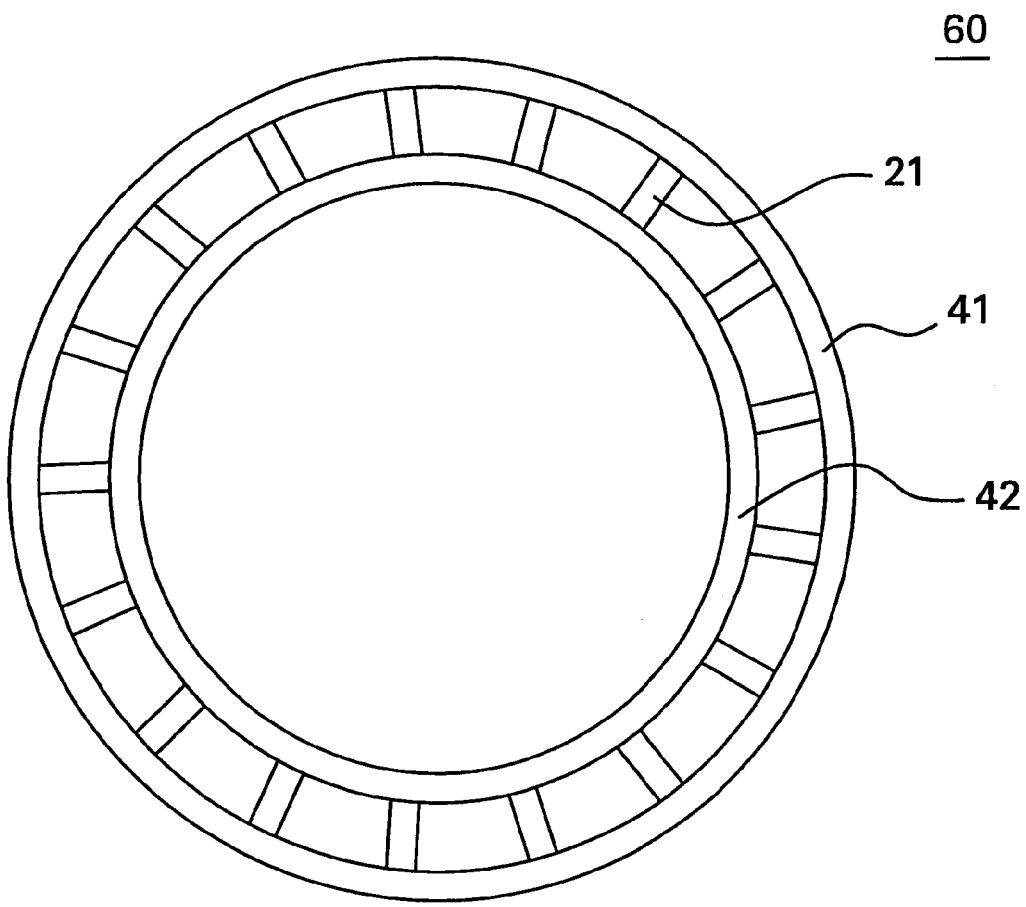
FIG. 2 schematically depicts basic elements of a stationary turbine nozzle assembly, in cross-sectional view.
Figure 3:
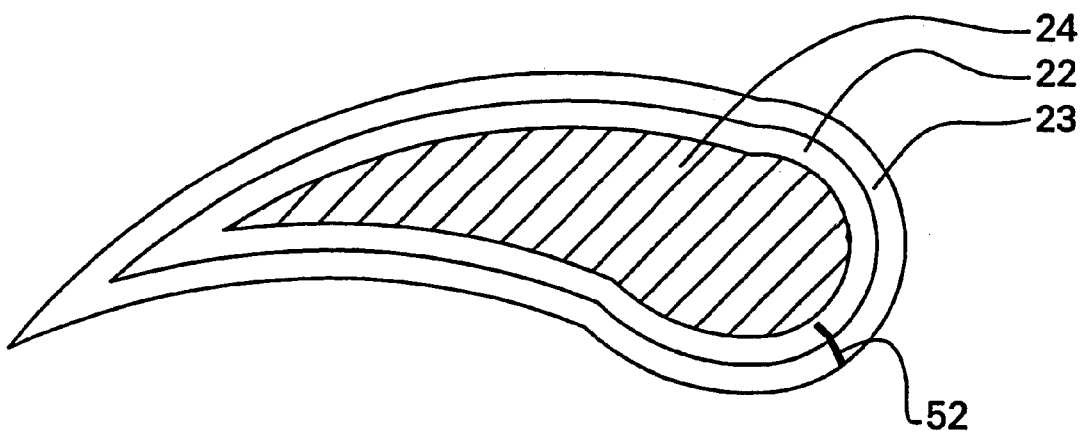
FIG. 3 illustrates an exemplary airfoil, in cross-sectional view.

Advantageously, the above-described method for in-situ eddy current inspection can be used to inspect airfoils 20 mounted on rotor disk 30 and to inspect stationary vane airfoils 20 mounted within a turbine engine (not shown), which are illustrated in FIGS. 1 and 2, respectively. A particular method embodiment for in-situ eddy current inspection of at least one airfoil 20, includes applying a drive pulse to drive coil 12 positioned at measurement position 28 on outer surface 11 of airfoil 20, while airfoil 20 is mounted in a turbine engine (not shown). The inspection method further includes receiving a response signal with magnetic field sensor 14 positioned at measurement position 28, comparing the response signal with a reference signal to obtain a compared signal, and analyzing the compared signal for crack detection. If the presence of crack 52 is indicated, the inspection method further includes analyzing the compared signal to determine the depth of crack 52 in coating 22, and analyzing the compared signal to determine whether crack 52 has penetrated base metal 24. If penetration of crack 52 into base metal 24 is indicated, the method further includes analyzing the compared signal to determine the depth of crack 52 in base metal 24.

To perform the crack detection and crack depth determination, the in-situ eddy current inspection method further includes determining a measured value for the compared signal. For this particular embodiment, the analysis steps respectively include comparing the measured value with a predetermined characteristic value to determine the presence of crack 52 in coating 22 near measurement position 28, comparing the measured value with coating calibration data to determine the depth of crack 52 in coating 22, comparing the measured value with a threshold value to determine whether crack 52 has penetrated base metal 24, and comparing the measured value with base metal calibration data to determine the depth of crack 52 in base metal 24. Alternatively, the secondary peak embodiment discussed above is used to perform crack detection and crack depth determination.

For one application of this embodiment, airfoil 20 is one of a number of airfoils 20 mounted on rotor disk 30, which is attached to rotor 10 positioned in the turbine engine. For this embodiment, the in-situ inspection method further includes rotating rotor disk 30 to position drive coil 12 and magnetic field sensor 14 (or collectively, to position sensor unit 16) at a measurement position 28 on an outer surface of a second airfoil (also indicated by reference numeral 20), while the second airfoil 20 is mounted on rotor disk 30 in the turbine engine. According to a more particular embodiment, drive coil 12 and magnetic field sensor 14 (or collectively, sensor unit 16) are retracted prior to rotation of rotor disk 30, to protect sensor unit 16 from being damaged by an airfoil, and then are positioned on second airfoil 20.

The above-described inspection procedure is then repeated for the second airfoil 20 to determine whether a crack 52 is present near measurement position 28 in the second airfoil 20 and, if crack 52 is detected, to ascertain whether crack 52 has penetrated base metal 24 of the second airfoil 20, as explained above. According to a more particular embodiment, rotor 10 is rotated, and the inspection procedure is repeated a number of times to inspect a number of airfoils 20 mounted on rotor disk 30, for example to inspect each of airfoils 20 mounted on rotor disk 30. Rotating rotor 10 (and hence rotor disk 30) obviates the need to move drive coil 12 and magnetic field sensor 14 to the different airfoils 20 on rotor disk 30, thereby simplifying and expediting the inspection process.

Similarly, in order to inspect one of a number of stationary vane airfoils 20 mounted within the turbine engine (not shown), the in-situ eddy current inspection method according to another embodiment further includes moving drive coil 12 and magnetic field sensor 14 (or collectively, moving sensor unit 16) to a measurement position 28 on a second of the stationary vane airfoils 20. The above-described inspection procedure is then repeated for the second stationary vane airfoil 20 to determine whether a crack 52 is present near measurement position 28 in the second stationary vane airfoil 20, and if crack 52 is detected, to ascertain whether crack 52 has penetrated base metal 24, as explained above. Further, drive coil 12 and magnetic field sensor 14 (or collectively, sensor unit 16) are moved and the inspection procedure is repeated a number of times to inspect a number of stationary vane airfoils 20, for example to inspect each of the stationary vane airfoils 20.

Figure 8:
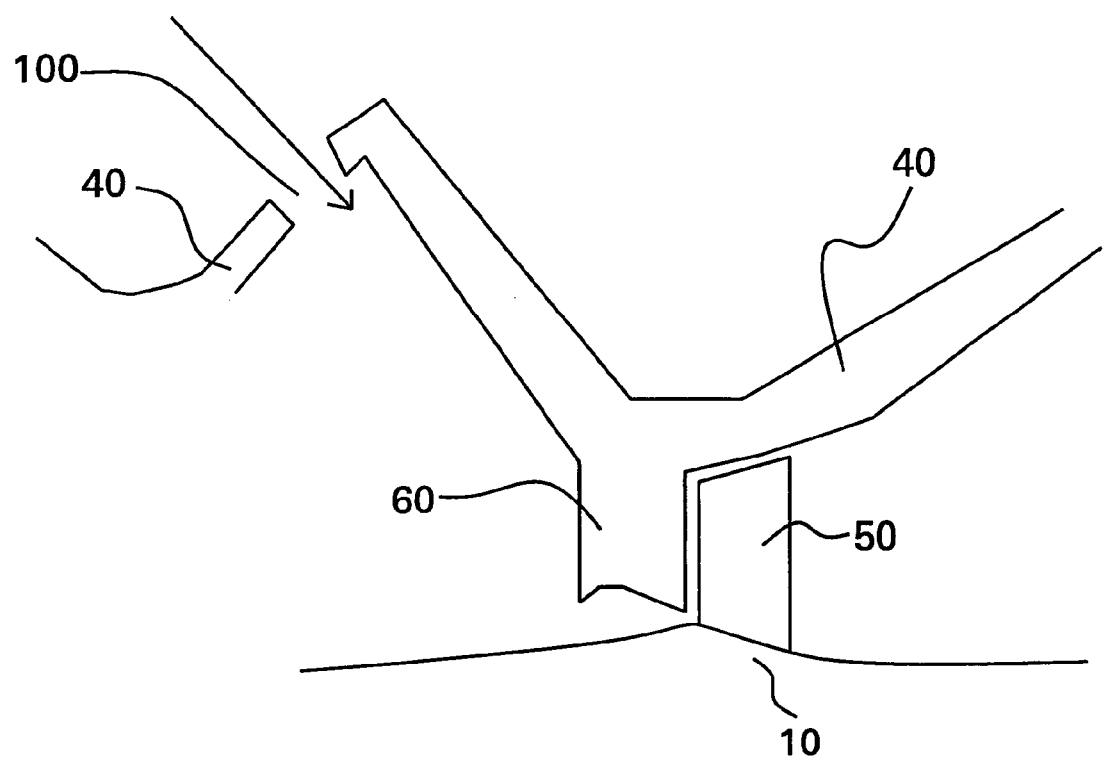
FIG. 8 shows an application of the in-situ inspection method to a gas turbine with a burner assembly, which includes fuel nozzles, an ignitor assembly, a burner can, and a transition piece, removed for insertion of a drive coil and a magnetic sensor.

In order to access the airfoils 20 mounted in the turbine engine, the in-situ eddy current inspection method according to a more specific embodiment further includes removing a burner assembly to create an entry port 100 in the turbine engine, as shown for example in FIG. 8. More precisely, entry port 100 provides access within case 40 to stationary turbine nozzle assembly 60 and rotor assembly 50, as illustrated in FIG. 8. The burner assembly (not shown) includes fuel nozzles (not shown), an ignitor assembly (not shown), a burner can (not shown), and a transition piece (not shown). Drive coil 12 and magnetic field sensor 14 are inserted through the entry port 100 for positioning at measurement position 28 on airfoil 20, and the inspection is performed as discussed above.

According to another embodiment, a method for eddy current inspection of coated component 20 is provided. The method includes applying a drive pulse at measurement position 28 on outer surface 11 of coated component 20 and receiving a response signal with magnetic field sensor 14 positioned at measurement position 28, as illustrated in FIG. 4. The method further includes comparing the response signal with a reference signal to obtain a compared signal and determining whether the compared signal includes a secondary peak P2 to determine whether a flaw (indicated by reference number 52) is present in coated component 20 near measurement position 28. As noted above, exemplary compared signals are shown in FIG. 5 and the second signal S2 includes a secondary peak P2, indicating the presence of flaw 52 near measurement position 28.

According to a particular embodiment, the eddy current inspection method further includes digitizing the reference signal to obtain a digitized reference signal and digitizing the response signal to obtain a digitized response signal. Exemplary digitization means include analog-to-digital converter 82, shown in FIG. 4. In addition, the digitized reference signal is subtracted from the digitized response signal to obtain the compared signal. According to a more particular embodiment, the eddy current inspection method is performed in-situ, namely while the coated component 20, for example airfoil 20, is installed in its operational environment, for example while airfoil 20 is mounted in a turbine engine (not shown).

To assess the scale of the damage to a cracked coated component, base metal penetration is ascertained, if the presence of the flaw is indicated. More particularly, a signature value is determined for the secondary peak, such as the time t at which the secondary peak P2 appears on the compared signal or the peak amplitude V of the secondary peak. The signature value is compared with a threshold value to determine whether flaw 52 has penetrated base metal 24, as discussed above. Exemplary threshold values include $V_{th}$ and $t_{th}$, as illustrated in FIG. 7 and discussed above.

In order to obtain more reliable inspection data, it is further desirable to perform a number of measurements at measurement position 28 and average the results to obtain the compared signal, as discussed above.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method for in-situ eddy current inspection of at least one coated component, the coated component comprising a base metal and a coating disposed on the base metal, said method comprising:

applying a drive pulse at a measurement position on an outer surface of the coated component while the coated component is installed in an operational environment of the coated component;

receiving a response signal from the coated component;

comparing the response signal with a reference signal to obtain a compared signal;

analyzing the compared signal for crack detection; and determining whether a crack near the measurement position has penetrated into the base metal, if the presence of the crack in the coating is indicated.

2. The in-situ eddy current inspection method of claim 1, wherein said application of the drive pulse comprises energizing a drive coil with the drive pulse, the drive coil being positioned at the measurement position, and wherein said reception of the response signal comprises receiving the response signal with a magnetic field sensor positioned at the measurement position.

3. The in-situ eddy current inspection method of claim 2, wherein the drive pulse comprises a rectangular wave pulse and has a pulse width of about 10 μs to about 100 μs.

4. The in-situ eddy current inspection method of claim 2, wherein said comparison comprises subtracting the reference signal from the response signal to obtain the compared signal.

5. The in-situ eddy current inspection method of claim 4, further comprising:

obtaining the reference signal using a reference sample, the reference signal being obtained by applying a drive pulse at a reference position on an outer surface of the reference sample and receiving the reference signal with the magnetic field sensor; and storing the reference signal.

6. The in-situ eddy current inspection method of claim 4, further comprising:

applying a reference drive pulse at a same-sample reference position on the coated component, while the coated component is installed in the operational environment; and receiving the reference signal with a reference magnetic field sensor positioned at the same-sample reference position.

7. The in-situ eddy current inspection method of claim 4, further comprising:

digitizing the reference signal to obtain a digitized reference signal; and digitizing the response signal to obtain a digitized response signal, wherein said comparison comprises subtracting the digitized reference signal from the digitized response signal to obtain the compared signal.

8. A method for in-situ eddy current inspection of at least one coated component, the coated component comprising a base metal and a coating disposed on the base metal, said method comprising:

applying a drive pulse at a measurement position on an outer surface of the coated component while the coated component is installed in an operational environment of the coated component, said application of the drive pulse comprising energizing a drive coil with the drive pulse, the drive coil being positioned at the measurement position;

receiving a response signal from the coated component with a magnetic field sensor positioned at the measurement position;

comparing the response signal with a reference signal to obtain a compared signal, said comparison comprising subtracting the reference signal from the response signal to obtain the compared signal;

analyzing the compared signal for crack detection;

determining whether a crack near the measurement position has penetrated into the base metal, if the presence of the crack in the coating is indicated;

digitizing the reference signal to obtain a digitized reference signal; and digitizing the response signal to obtain a digitized response signal, where in said comparison comprises subtracting the digitized reference signal from the digitized response signal to obtain the compared signal, wherein said crack detection analysis comprises:

extracting a measured value from the compared signal, and comparing the measured value with a predetermined characteristic value to determine the presence of a crack near the measurement position, and wherein said determination of whether the crack has penetrated into the base metal comprises comparing the measured value with a threshold value.

9. The in-situ eddy current inspection method of claim 8, wherein the measured value and the threshold value comprise one of a time value and a peak amplitude value.

10. The in-situ eddy current inspection method of claim 8, further comprising determining the depth of the crack in the coating, if the presence of the crack near the measurement position is indicated.

11. The in-situ eddy current inspection method of claim 10, wherein said determination of the depth of the crack in the coating comprises comparing the measured value with coating calibration data.

12. The in-situ eddy current inspection method of claim 10, further comprising determining the depth of the crack in the base metal, if penetration of the base metal is indicated.

13. The in-situ eddy current inspection method of claim 12, wherein said determination of the depth of the crack in the base metal comprises comparing the measured value with base metal calibration data.

14. The in-situ eddy current inspection method of claim 8, further comprising:

repeating said application and said reception to obtain a plurality of response signals with the magnetic field sensor positioned at the measurement position, wherein said digitization comprises digitizing the response signals to obtain a plurality of digitized signals, and wherein said comparison comprises:

subtracting the digitized reference signal from each of the digitized signals to obtain a plurality of digitized compared signals; and averaging the digitized compared signals to obtain the compared signal.

15. The in-situ eddy current inspection method of claim 8, further comprising repeating said application and said reception to obtain a plurality of response signals with the magnetic field sensor positioned at the measurement position, wherein said digitization comprises:

digitizing the response signals to obtain a plurality of digitized signals, averaging the digitized signals to obtain the digitized response signal.

16. A method for in-situ eddy current inspection of at least one airfoil, the airfoil comprising a base metal and a coating disposed on the base metal, said method comprising:

(a) applying a drive pulse to a drive coil positioned at a measurement position on an outer surface of the airfoil while the airfoil is mounted in a turbine engine;

(b) receiving a response signal with a magnetic field sensor positioned at the measurement position (c) comparing the response signal with a reference signal to obtain a compared signal;

(d) analyzing the compared signal for crack detection;

(e) analyzing the compared signal to determine the depth of a crack in the coating near the measurement position, if the presence of the crack is indicated;

(f) analyzing the compared signal to determine whether the crack has penetrated the base metal, if the presence of the crack is indicated; and (g) analyzing the compared signal to determine the depth of the crack in the base metal, if penetration of the crack into the base metal is indicated.

17. A method for in-situ eddy current inspection, of at least one airfoil, the airfoil comprising a base metal and a coating disposed on the base metal, said method comprising:

(a) applying a drive pulse to a drive coil positioned at a measurement position on an outer surface of the airfoil while the airfoil is mounted in a turbine engine;

(b) receiving a response signal with a magnetic field sensor positioned at the measurement position;

(c) comparing the response signal with a reference signal to obtain a compared signal;

(d) analyzing the compared signal for crack detection;

(e) analyzing the compared signal to determine the depth of a crack in the coating near the measurement position, if the presence of the crack is indicated;

(f) analyzing the compared signal to determine whether the crack has penetrated the base metal, if the presence of the crack is indicated;

(g) analyzing the compared signal to determine the depth of the crack in the base metal, if penetration of the crack into the base metal is indicated; and (h) extracting a measured value from the compared signal, wherein steps (d)–(g) respectively comprise:

(d) comparing the measured value with a predetermined characteristic value to determine the presence of the crack in the coating near the measurement position, (e) comparing the measured value with coating calibration data to determine the depth of the crack in the coating, (f) comparing the measured value with a threshold value to determine whether the crack has penetrated into the base metal, and (g) comparing the measured value with base metal calibration data to determine the depth of the crack in the base metal.

18. A method for in-situ eddy current inspection of at least one airfoil, the airfoil comprising a base metal and a coating disposed on the base metal, wherein the airfoil is one of a plurality of airfoils mounted on a rotor disk which is attached to a rotor positioned in the turbine engine, said method comprising:

(a) applying a drive pulse to a drive coil positioned at a measurement position on an outer surface of the airfoil while the airfoil is mounted in a turbine engine;

(b) receiving a response signal with a magnetic field sensor positioned at the measurement position;

(c) comparing the response signal with a reference signal to obtain a compared signal;

(d) analyzing the compared signal for crack detection;

(e) analyzing the compared signal to determine the depth of a crack in the coating near the measurement position, if the presence of the crack is indicated;

(f) analyzing the compared signal to determine whether the crack has penetrated the base metal, if the presence of the crack is indicated;

(g) analyzing the compared signal to determine the depth of the crack in the base metal, if penetration of the crack into the base metal is indicated;

(h) rotating the rotor disk to position the drive coil and the magnetic field sensor at a measurement position on an outer surface of a second of the airfoils, while the second airfoil is mounted on the rotor disk in the turbine engine; and repeating steps (a)–(g) for the second airfoil.

19. The in-situ eddy current inspection method of claim 18, wherein said rotation of the rotor disk and said repetition of steps (a)–(g) are performed for each of the airfoils mounted on the rotor disk.

20. A method for in-situ eddy current inspection of at least one airfoil, the airfoil comprising a base metal and a coating disposed on the base metal, wherein the airfoil is one of a plurality of stationary vane airfoils mounted within the turbine engine, said method comprising:

(a) applying a drive pulse to a drive coil positioned at a measurement position on an outer surface of the airfoil while the airfoil is mounted in a turbine engine;

(b) receiving a response signal with a magnetic field sensor positioned at the measurement position;

(c) comparing the response signal with a reference signal to obtain a compared signal;

(d) analyzing the compared signal for crack detection;

(e) analyzing the compared signal to determine the depth of a crack in the coating near the measurement position, if the presence of the crack is indicated;

(f) analyzing the compared signal to determine whether the crack has penetrated the base metal, if the presence of the crack is indicated;

(g) analyzing the compared signal to determine the depth of the crack in the base metal, if penetration of the crack into the base metal is indicated;

(h) moving the drive coil and the magnetic field sensor to a measurement position on a second of the stationary vane airfoils; and repeating steps (a)–(g) for the second stationary vane airfoil.

21. The in-situ eddy current inspection method of claim 20, wherein said movement of the drive coil and the magnetic field sensor and said repetition of steps (a)–(g) are performed for each of the stationary vane airfoils.

22. A method for in-situ eddy current inspection of at least one airfoil, the airfoil comprising a base metal and a coating disposed on the base metal, said method comprising:

(a) applying a drive pulse to a drive coil positioned at a measurement position on an outer surface of the airfoil while the airfoil is mounted in a turbine engine;

(b) receiving a response signal with a magnetic field sensor positioned at the measurement position;

(c) comparing the response signal with a reference signal to obtain a compared signal;

(d) analyzing the compared signal for crack detection;

(e) analyzing the compared signal to determine the depth of a crack in the coating near the measurement position, if the presence of the crack is indicated;

(f) analyzing the compared signal to determine whether the crack has penetrated the base metal, if the presence of the crack is indicated;

(g) analyzing the compared signal to determine the depth of the crack in the base metal, if penetration of the crack into the base metal is indicated;

(h) creating an entry port in the turbine engine; and (i) inserting the drive coil and the magnetic field sensor through the entry port, wherein said insertion is performed prior to positioning the drive coil and the magnetic field sensor at the measurement position on the airfoil.

23. A method for eddy current inspection of a coated component comprising a base metal and a coating disposed on the base metal, said method comprising:

applying a drive pulse to a drive coil at a measurement position on an outer surface of the coated component;

receiving a response signal with a magnetic field sensor positioned at the measurement position;

comparing the response signal with a reference signal to obtain a compared signal; and determining whether the compared signal includes a secondary peak to ascertain whether a flaw is present in the coated component near the measurement position.

24. The eddy current inspection method of claim 23, further comprising:

digitizing the reference signal to obtain a digitized reference signal; and digitizing the response signal to obtain a digitized response signal, wherein said comparison comprises subtracting the digitized reference signal from the digitized response signal to obtain the compared signal.

25. The eddy current inspection method of claim 24, further comprising ascertaining base metal penetration, if said determination indicates the presence of the flaw, said ascertainment comprising:

determining a signature value for the secondary peak, and comparing the signature value with a threshold value to determine whether the flaw has penetrated the base metal.

26. The eddy current inspection method of claim 24, further comprising repeating said application and said reception to obtain a plurality of response signals with the magnetic field sensor positioned at the measurement position, wherein said digitization comprises:

digitizing the response signals to obtain a plurality of digitized signals;

averaging the digitized signals to obtain the digitized response signal.

27. The eddy current inspection method of claim 24, further comprising repeating said application and said reception to obtain a plurality of response signals with the magnetic field sensor positioned at the measurement position, wherein said digitization comprises digitizing the response signals to obtain a plurality of digitized signals, and wherein said comparison comprises:

subtracting the digitized reference signal from each of the digitized signals to obtain a plurality of digitized compared signals, and averaging the digitized compared signals to obtain the compared signal.

28. The eddy current inspection method of claim 24, wherein the coated component comprises an airfoil, and said application and reception are performed while the airfoil is mounted in a turbine engine.

29. A method for eddy current inspection of a coated component comprising a base metal and a coating disposed on the base metal, said method comprising:

(a) applying a drive pulse to a drive coil at a measurement position on an outer surface of the coated component;

(b) receiving a response signal with a magnetic field sensor positioned at the measurement position;

(c) comparing the response signal with a reference signal to obtain a compared signal;

(d) determining whether the compared signal includes a secondary peak to ascertain whether a flaw is present in the coated component near the measurement position; and, if the presence of the flaw is indicated, further comprising:

(e) determining a signature value for the secondary peak; and (f) comparing the signature value with a threshold value to determine whether the flaw has penetrated into the base metal.

30. The eddy current inspection method of claim 29, wherein the coated component comprises an airfoil, and steps (a) and (b) are performed while the airfoil is mounted in a turbine engine.

* * * * *